United States Patent [19]

Birnboim et al.

[11] Patent Number: 5,023,139
[45] Date of Patent: Jun. 11, 1991

[54] NONLINEAR OPTICAL MATERIALS

[75] Inventors: Meyer H. Birnboim, Troy, N.Y.; Arthur E. Neeves, Gillette, N.J.

[73] Assignee: Research Corporation Technologies, Inc., Tucson, Ariz.

[21] Appl. No.: 418,057

[22] Filed: Oct. 6, 1989

Related U.S. Application Data

[63] Continuation of Ser. No. 333,157, Apr. 4, 1989.

[51] Int. Cl.$^5$ .................................................. B32B 9/00
[52] U.S. Cl. .................................... 428/402; 428/403; 428/64; 428/913
[58] Field of Search .................... 428/64, 402, 403; 369/288; 252/582, 589, 600; 350/354, 393, 96.12

[56] References Cited

U.S. PATENT DOCUMENTS

| | | | |
|---|---|---|---|
| 4,649,280 | 3/1987 | Holland et al. | 250/483.1 |
| 4,659,177 | 4/1987 | Choe et al. | 428/411.1 |
| 4,707,305 | 11/1987 | Choe et al. | 548/300 |
| 4,716,449 | 12/1987 | Miller | 357/30 |
| 4,732,783 | 3/1988 | Choe et al. | 427/164 |
| 4,764,429 | 8/1988 | Mair | 428/403 |
| 4,767,169 | 8/1988 | Teng et al. | 350/96.12 |
| 4,773,743 | 9/1988 | Choe et al. | 350/393 |
| 4,774,025 | 9/1988 | Choe et al. | 252/600 |
| 4,775,215 | 10/1988 | Teng et al. | 350/96.34 |
| 4,801,659 | 1/1989 | Leslie | 252/582 |
| 4,807,968 | 2/1989 | Leslie | 252/600 |
| 4,824,219 | 4/1989 | Choe | 350/354 |
| 4,855,078 | 8/1989 | Leslie | 252/600 |
| 4,855,376 | 8/1989 | DeMartino et al. | 252/600 |
| 4,877,298 | 10/1989 | Teng et al. | 350/96.14 |
| 4,882,402 | 11/1989 | Leslie et al. | 252/582 |
| 4,887,889 | 12/1989 | Leslie | 252/600 |
| 4,892,682 | 1/1990 | DeMartino et al. | 252/600 |
| 4,898,691 | 2/1990 | Borzo et al. | 252/600 |
| 4,906,407 | 3/1990 | DeMartino et al. | 252/589 |

FOREIGN PATENT DOCUMENTS

0154504 2/1985 European Pat. Off. .
3134602 6/1988 Japan .
8800526 1/1988 World Int. Prop. O. .

OTHER PUBLICATIONS

Polarization Selective Optical Phase Conjugation in a Kerr-Like Medium, A. E. Neeves et al., Rensselaer Polytechnic Institute, vol. 5, No. 3, J. Opt. Soc. Am. B, pp. 701–708: 1988.

Elastic Scattering, Absorption, and Surface-Enhanced Raman Scattering by Concentric Spheres Comprised of a Metallic and a Dielectric Region, M. Kerker et al., Clarkson College of Technology, vol. 26, No. 8, The American Physical Society, pp. 4052–4063; 1982.

Nonlinear Optics at Surfaces and in Composite Materials, D. Ricard, pp. 154–178, Nonlinear Optics: Materials and Devices, Flytzanis and Oudar, eds., 1985.

Optical Nonlinearities of Small Metal Particles: Surface-Mediated Resonance and Quantum Size Effects, F. Hache et al., vol. 3, No. 12, J. Opt. Soc. Am. B, pp. 1647–1655, 1986.

Surface-Mediated Enhancement of Optical Phase Conjugation in Metal Colloids, D. Ricard et al., vol. 10, No. 5, Optics Letters, Opt. Soc. of Am., pp. 511–513; 1985.

List continue on next page.

Primary Examiner—Patrick J. Ryan
Attorney, Agent, or Firm—Scully, Scott, Murphy & Presser

[57] ABSTRACT

Particles comprising a core surrounded by at least one shell wherein at least one of the core or one of the shells is a metal and at least one of the core or one of the shells is a dielectric material which exhibits a third order nonlinear response. The "shell" of a metal particle may be the adjacent region of a medium in which said particle is suspended, said medium having a third order nonlinear response. In a preferred embodiment, the particles are suspended in a dielectric medium that may be linear or may exhibit a third order nonlinear response. Enhancement of the effective $\chi^{(3)}$ of the particles and suspensions result from the concentration of the electric field in and around the particles at the plasmon resonance frequency of the metal.

52 Claims, 7 Drawing Sheets

Phase Conjugation in Liquid Suspensions of Microspheres in the Diffusive Limit, D. Rogovin et al., Rockwell International, Science Center, vol. 31, No. 4, The Am. Phys. Soc., pp. 2375–2389; 1985.

Four-Wave Mixing in an Artificial Kerr Medium, P. W. Smith et al., Optical Soc. of Am., Optics Letters, vol. 6, No. 6, pp. 284–286, 1981.

What is Phase Conjugation and What Does it Do?, A. Yariv et al.

Optical Phase Conjugation, Chapter 1; pp. 2–4; 1983.

Surface Modes in Small Spheres, C. F. Bohren et al., Absorption and Scattering of Light by Small Particles, Chapter 12, pp. 335–336.

The Physics of Phase Conjugate Mirrors, M. C. Gower, Prog. Quant. Electr., vol. 9, pp. 101–147; 1984.

Surface Plasmons in Small Layer Metal Particles, A. A. Lushnikow et al., vol. 20, Solid State Communications, pp. 545–547; 1976.

Extinction Coefficients for a Random Dispersion of Small Stratified Spheres and a Random Dispersion of Their Binary Aggregates, F. Borghese et al., vol. 4, No. 10, J. Opt. Soc. Am. A, pp. 1984–1991; 1987.

Absorption Spectrum of Clusters of Spheres from the General Solution of Maxwell's Equations, III, Heterogeneous Spheres, J. M. Gerardy, vol. 30, No. 4, Physical Review B, pp. 2164–2181; 1983.

Raman and Fluorescent Scattering by Molecules Embedded in Concentric Spheres, H. Chew et al., vol. 66, No. 5, J. Opt. Soc. Am., pp. 440–444; 1975.

NONLINEAR OPTICAL MATERIALS

This application is a continuation application of prior application Ser. No. 333,157, filed on Apr. 4, 1989.

BACKGROUND OF THE INVENTION a) Field of the Invention

The present invention relates to optical devices formed by metallic particles suspended in a medium, and more particularly, to such devices which exhibit third order non-linear susceptibility.

b) Summary of the Prior Art

Nonlinear optical materials are central to optical domain computing as real time holographic and bistable memory devices, as optical correlator devices, as phase conjugator devices and as thresholding devices. A number of fast response time polymeric and semiconductor materials have emerged that have electronic nonlinear mechanisms in the picosecond and subpicosecond time scale. However the small magnitude of the optical nonlinearity requires a high laser density to utilize these materials. The consequent power dissipation limits the utilization of these materials.

Optical phase conjugation has been measured from dilute linear suspensions of nonlinear nanospheres in degenerate four wave mixing experiments. In "Phase Conjugation in Liquid Suspensions of Microspheres in the Diffusive Limit," 31 Phys. Rev. A. 2375 (1985), Rogovin and Sari attributed the apparent third order optical susceptibility, $X^{(3)}$, to a slow electrostrictive mechanism for dielectric spheres in a dilute suspension. See also Smith et al., "Four-wave Mixing in an Artificial Kerr Medium," 6 Optics Letters 284 (1985), and Neeves et al., "Polarization Selective Optical phase Conjugation in a Kerr-like Medium," 5 Opt. Soc. Am., B 701 (1988). These suspensions suffer from slow response time and grating instabilities that give rise to a poor signal to noise ratio.

On the other hand, in "Optical Nonlinearities of Small Metal Particles: Surface-mediated Resonance and Quantum Size Effect," 3 J. Opt. Soc. Am. B 1647 (1986), Hache et al. attributed the apparent $\chi^{(3)}$ of metal spheres in a dilute suspension in a linear dielectric medium to a fast electronic mechanism. See also Ricard et al. "Surface-mediated Enhancement of Optical Phase Conjugation in Metal Colloids," 10 Optics Letters 511 (1985). For this case the effective $\chi^{(3)}$ is enhanced at the surface mediated plasmon resonance frequency.

Some metallic suspensions therefore have a fast response and an effective optical nonlinearity with large magnitude. However, due to the large dielectric loss, the figure of merit for nonlinear composite materials is relatively poor. The figure of merit is defined as the ratio of $\chi^{(3)}$ to the optical absorption for the material.

SUMMARY OF THE PRESENT INVENTION

The present invention is directed to particles comprising a core surrounded by at least one shell wherein at least the core or one of the shells is a metal and at least the core or one of the shells is a dielectric material which exhibits a nonlinear optical response. The core and the shells are also referred to as the "layers" of the particle. Thus, at least one of the layers of the particle is a metal and at least one of the layers which are not metal is made of dielectric material which exhibit a third order nonlinear response. The particles may be any shape, but they are usually nanoparticles, i.e., have dimensions on the order of nanometers.

A nanoparticles of the present invention will exhibit an effective third order nonlinear response. The effective third order nonlinear response is the response of the particle considered as a whole and results from the third order nonlinear response of its constituent core and shells. At one or more optical frequencies the particle exhibits an "enhanced" third order nonlinear response. That is, its effective third order nonlinear response is much greater than the sum of the nonlinear responses of each of the core and shells separately at the same optical frequency.

"Nonlinear" as the term is used in the present invention refers to the optical response of a material. Nonlinear optical response occurs when a material exhibits hyperpolarization on a molecular level. Theoretically all materials can exhibit hyperpolarization and thus nonlinear optical responses. However the intensity of radiation required to hyperpolarize a material distinguishes them into well defined categories of "linear" and "nonlinear" materials, known to those skilled in the art.

The present invention is also directed to composite materials formed with the particles in a medium in which either the particles or the medium includes a dielectric material exhibiting a third order nonlinear optical response. The materials of the invention may comprise the layered particles described above in a medium where the medium is either linear or nonlinear. The composite material may also be formed with a unitary metallic particle in a nonlinear medium where the medium surrounding the particle acts as the shell layer.

The enhanced third order nonlinear response of the particles of the present invention at one or more optical frequencies arises when one of the metal layers mediates a plasmon resonance. The condition for plasmon resonance of the metal layer depends on order, number, shape and the dimensions of the particle's layers, the material of the layers, as well as the nature of the medium surrounding the particle. The one or more optical frequencies at which the particle exhibits enhanced nonlinear response and, necessarily, at which any one of the metal-dielectric layers exhibits plasmon resonance is referred to as the plasmon resonance frequency of the particle.

At the plasmon resonance, the electric field of the incident light concentrates in and around the particle. "Concentration" of the electric field refers to the intensity of the light in and around the particle with respect to the intensity of light in and around an identical particle without the metal layer exhibiting plasmon resonance. The concentrated electric field in the particle layers serves to increase their degree of polarization and therefore their nonlinear optical response. Thus, the nonlinear optical response of the particle is enhanced as that term is defined above.

The enhanced third order nonlinear response results in an increased polarization. Those skilled in the art attribute the increased polarization to a number of different mechanisms; the response of different types of materials being more or less attributed to these different mechanisms. For example, metals exhibit an increased polarization predominantly due to an electronic mechanism. Other materials exhibit an increased polarization due to an excitonic mechanism or thermal mechanism or others. Some exhibit an electrostrictive mechanism.

Considering the specific particle with a metal core and a nonlinear dielectric shell, the "shell" may be the immediately adjacent portion of a nonlinear dielectric medium or matrix in which a metal nanoparticle is suspended. The enhancement of $\chi^{(3)}$ takes place in a localized region that for a nanosphere extends into the medium by approximately two particle diameters. Thus, the particle can be thought of as a core and shell suspended in a medium, the shell and medium being the same nonlinear dielectric material.

The present invention provides a particle with enhanced third order nonlinear susceptibility, fast response time and an enhanced figure of merit. The enhanced $\chi^{(3)}$ and figure of merit for the electronic mechanism of the particles of the present invention have been determined theoretically and have experimental support. It also has the added feature of enhancing the third order nonlinear susceptibility of the suspension medium in the vicinity of the material.

In one embodiment of the present invention, the composite material is formed with a plurality of particles consisting of a metallic core surrounded with a nonlinear dielectric shell material and suspended in a nonlinear dielectric medium. The field in the vicinity of each of the particles is larger than the mean field through the structure. Since each region of the structure has independent intrinsic $\chi^{(3)}$ nonlinearities, this results in an enhancement of the optical nonlinearity from each component of the suspension as a consequence of the localized electric field effect. The "enhancement" of the composite material may therefore be considered as the ratio of $\chi^{(3)}$ for a homogeneous suspension medium to $\chi^{(3)}$ for a suspension medium with the particle suspended therein. By suitable matching of the core, shell and suspension medium dielectric functions, the resonance will exhibit broad band enhancement.

The enhancement of $\chi^{(3)}$ takes place in a localized region that, for a spherical particle, extends to about two particle diameters. While the enhancement can be enormous in this localized region for each particle, the effective enhancement of the composite material is reduced by the concentration effect when averaged over the entire material. Nevertheless, enhancements of $10^4$ for the material are predicted even after averaging.

Thus, the composite material of the present invention, when the suspension medium is a nonlinear dielectric, can be conceptualized as a multiple of the particles with another "shell" surrounding the outermost shell of the particle with dielectric permittivity equal to that of the suspension medium.

In another embodiment of the present invention, the composite material is formed with optical particles consisting of a nonlinear dielectric core surrounded with a metallic shell and suspended in a nonlinear dielectric medium. With this structure a large spectral resonant frequency range can be achieved through adjustment of shell thickness even with a single metal and still derive large field enhancement. Again, the particles exhibit increased polarization one or more resonant frequencies in the optical spectrum and, as a result, the effective third order nonlinear susceptibility of the suspension is enhanced at those resonant frequencies.

The nanoparticles of the present invention are not limited to any particular geometric configuration. The particles may comprise, for example, a spherical core with spherical shells, an ellipsoidal core with ellipsoidal shells or a cylindrical core with cylindrical shells. These are referred to as nanospheres, nanoellipsoids and nanocylinders, i.e., spheres, ellipsoids and cylinders with dimensions on the order of nanometers. The underlying concept of the invention is that a uniform optical field in a homogeneous material can be converted to a non-uniform optical field by replacing the homogeneous structure by an equivalent inhomogeneous structure. The field is localized and further enhanced by a surface mediated plasmon resonance. Nonlinear effects in the structure can be enhanced relative to the homogeneous structure.

DETAILED DESCRIPTION OF THE PREFERRED EMBODIMENT

Figure 1:
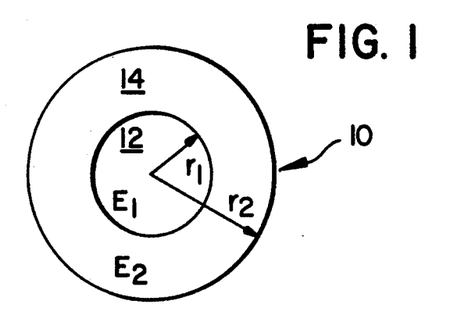
FIGS. 1-3, not to scale, show particle of the present invention.

Referring to FIG. 1, a particle 10 of the present invention is shown, not drawn to scale. The particle 10 is a nanosphere and consists of a core 12 of radius $r_1$, and dielectric permittivity $\epsilon_1$ surrounded by one shell 14 of radius $r_2$ and dielectric permittivity $\epsilon_2$. In one embodiment, the core 12 is a metal and the shell 14 is a dielectric material which exhibits a third order nonlinear response. In a second embodiment, the shell 14 is a metal and the core 12 is a dielectric material exhibiting a third order nonlinear response.

In both embodiments, the particle exhibits an effective third order nonlinear response which is enhanced at one or more frequencies of incident optical light.

Figure 2:
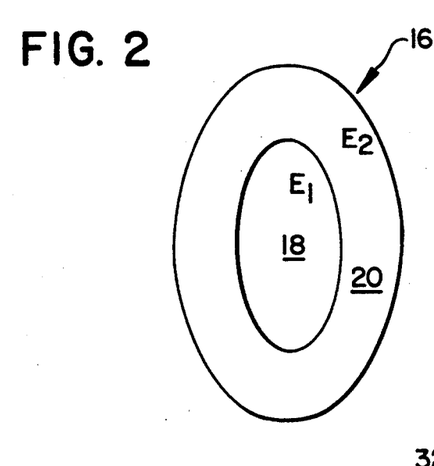

In FIG. 2, another embodiment of a particle 16 of the present invention is shown, again not to scale. The particle 16 is a nanoellipsoid with core 18 of dielectric permittivity $\epsilon_1$ and shell 20 of dielectric permittivity $\epsilon_2$. The core 18 may be a metal and the shell 20 may be a dielectric exhibiting a nonlinear optical response, or vice versa. The shape asymmetry with high curvature will further enhance the localized field and gives rise to three non-degenerate resonant modes.

Figure 3:
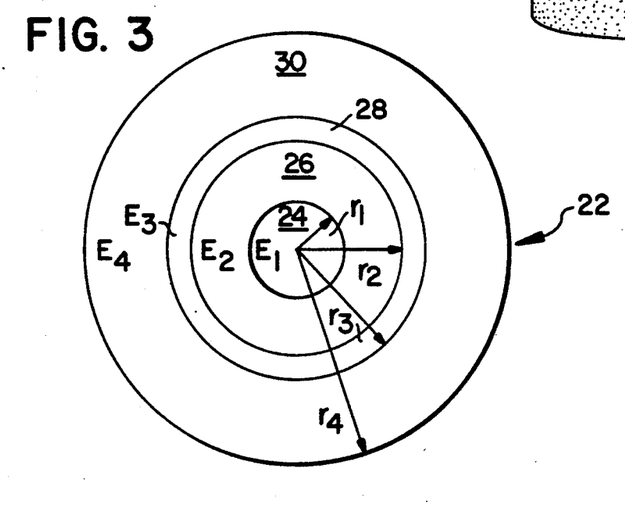

Referring to FIG. 3, a particles 22 with multiple shells is shown, again not to scale. The particle 22 is a nanosphere with a core and three shells 26, 28, 30 of dielectric permittivity $\epsilon_1$, $\epsilon_2$, $\epsilon_3$ and $\epsilon_4$ respectively, and radii $r_1$, $r_2$, $r_3$ and $r_4$ respectively. The core 24 and shells 26, 28 and 30 comprise the layers of particles. At least one of the layers is a metal, and at least one of the layers is a dielectric material exhibiting a third order nonlinear response. In one embodiment layers 26 and 28 are metals and layers 26 and 30 are nonlinear dielectrics. In another embodiment layers 26 and 30 are metals while layers 24 and 28 are nonlinear dielectrics. In this embodiment a number of plasmon surface resonances of the metals will give rise to a number of surface resonance frequencies of the material, excluding the degenerate cases for certain shell thicknesses or $\epsilon$ adjustments.

The particles of the present invention are not limited to any particular number of shells or order of metal or dielectric among the shells. Also, the shape of the multiple shelled particles may be spherical, ellipsoidal, cylindrical or other shape. The core of the particle may be a metal and all of the surrounding shells may be nonlinear dielectric material or vice versa. Furthermore, a "superlattice" configuration of multiple shells is part of the present invention. That is, the adjacent layers of the particle alternate between metal and nonlinear dielectric material. In this embodiment, the metal layers will be relatively thin compared to the dielectric layers.

In the ensuing description, the particles, described in themselves above, are used to fabricate composite materials of the present invention. More specifically, the composite materials comprise suspensions of the particles described above. In other words, the particles themselves are surrounded by a medium itself having a dielectric permittivity. The medium is a dielectric material which may or may not exhibit a nonlinear optical response. The medium may be a liquid or a solid, and the solid may have a matrix structure. In the following description, the term "suspension" is equivalent to the term "material" and the term "suspension medium" is equivalent to the term "medium."

Figure 4:
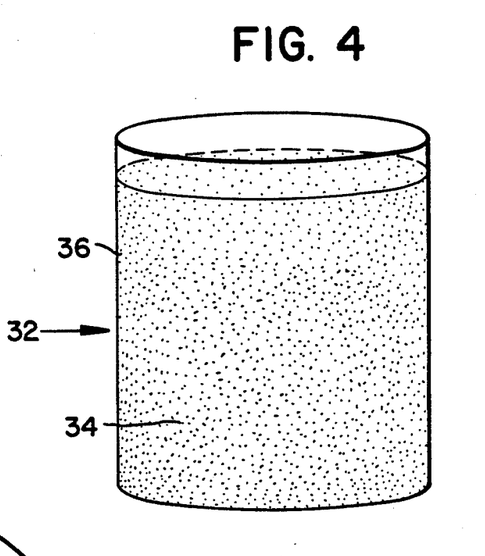
FIG. 4, also not to scale, shows a composite material of the present invention.

Referring to FIG. 4, a composite material 32 of the present invention is shown. The composite material 32 comprises particles 34 suspended in suspension medium 36.

In the first preferred embodiment, the particles 34 of the material 32 consists of nanospheres, i.e., spheres with dimensions on the order of $10^{-8}$ or $10^{-9}$m, with a metallic core, $\epsilon_1$, clad with a nonlinear shell material, $\epsilon_2$, and suspended in a nonlinear medium, $\epsilon_3$. Light of a frequency $\omega_R$ incident on the material satisfies the surface-mode resonance for the material and is further described below. The nanosphere must be chosen such that scattering does not significantly affect the figure of merit. Normally in three dimensional structures this means that all three dimensions of the nanoparticle must be much less than the wavelength of the incident light. For structures of essentially two or one dimension, only the two or one dimension must satisfy this condition.

The field in the interior and vicinity of the particles 34 is larger than the mean field through the material 32. Since each region of the material 32 has independent intrinsic $\chi^{(3)}$ nonlinearities, this results in an enhancement of the optical nonlinearity from each component of the suspension 32 as a consequence of the localized electric field effect.

The structure of the particles enables separation of the functions of the requisite negative dielectric permittivity provided by the metal from the intrinsic nonlinearity to be enhanced that can be provided by the metal or by any of the dielectrics.

The material therefore has enhanced third order nonlinear susceptibility at at least one optical wavelength. In the following treatment, suspensions are sufficiently dilute so that interparticle effects may be neglected. It is noted that at higher concentrations the field enhancement may be increased or decreased, but higher concentrations may promote intrinsic optical bistability in the composite material. The spatial dependence of the field strength for homogeneous optical particles for which the dielectric permittivity may be real, complex, and dispersive is described first, followed by consideration of the enhancements of phase conjugation expected from the electrostrictive contribution and from the electronic contribution to $\chi^{(3)}$ as a function of particle concentration.

The electric field distribution $E_1$, $E_2$ and $E_3$ is calculated for each region of the material, $\epsilon_1$, $\epsilon_2$ and $\epsilon_3$, within the electrostatic approximation relative to the electric field $E_o$ far from the particle and is plotted for some specific parameters in FIGS. 6a and 6b, described below. The field outside the particle is equivalent to that of a dipole of moment p, with an effective complex dielectric constant $\kappa_{eff}$ $$p = 4\pi \epsilon_3 r_2^3 \frac{(\kappa_{eff} - 1)}{(\kappa_{eff} + 2)} E_o \qquad (1)$$

$$\kappa_{eff} = \frac{\epsilon_2}{\epsilon_3} \frac{(\epsilon_1 - 2\epsilon_2) + 2(\epsilon_1 - \epsilon_2)\left(\frac{r_1}{r_2}\right)^3}{(\epsilon_1 + 2\epsilon_2) - (\epsilon_1 - \epsilon_2)\left(\frac{r_1}{r_2}\right)^3} \qquad (2)$$

The condition for surface-mode resonance $\omega_R$ is defined for the composite by $$\kappa'_{eff} + 2 = 0 \qquad (3)$$

The theoretical dielectric function, $\epsilon_1(\omega)$, for a metallic core that exhibits anomalous dispersion with the requisite negative real component of the dielectric permittivity of the core $\epsilon_1'$ required to satisfy the surface resonance condition may be represented in the frequency range of interest by the classical Drude free electron or alternatively by a combined Drude free electron model in combination with the Lorentz oscillator model for the bound electron contribution. Gold particles at optical energies that exceed the threshold of 2 eV for interband transitions, require a dielectric function that must include both the free electron (intraband) and the bound electron (interband) contributions. Above this threshold energy the form of the curve of the imaginary component of the dielectric permittivity of the core, $\epsilon''$, in particular, depends on the specific band structure of the material. The values for the parameters $\omega_p$, plasmon frequency, $\omega_o$, bound electron frequency, $\tau_f$, free electron decay time, and $\tau_b$, bound electron decay time, in the combined model are based on the fit to the experimental data, including the size dependence of $\tau_f$. Aluminum is a material whose dielectric properties are well described by the free electron model in the ultraviolet except for a weak bound contribution near 1.5 eV. The choice of values for the parameters $\omega_p$ and $\tau_f$ in the Drude model are based on fit to experimental data.

Figure 5A:
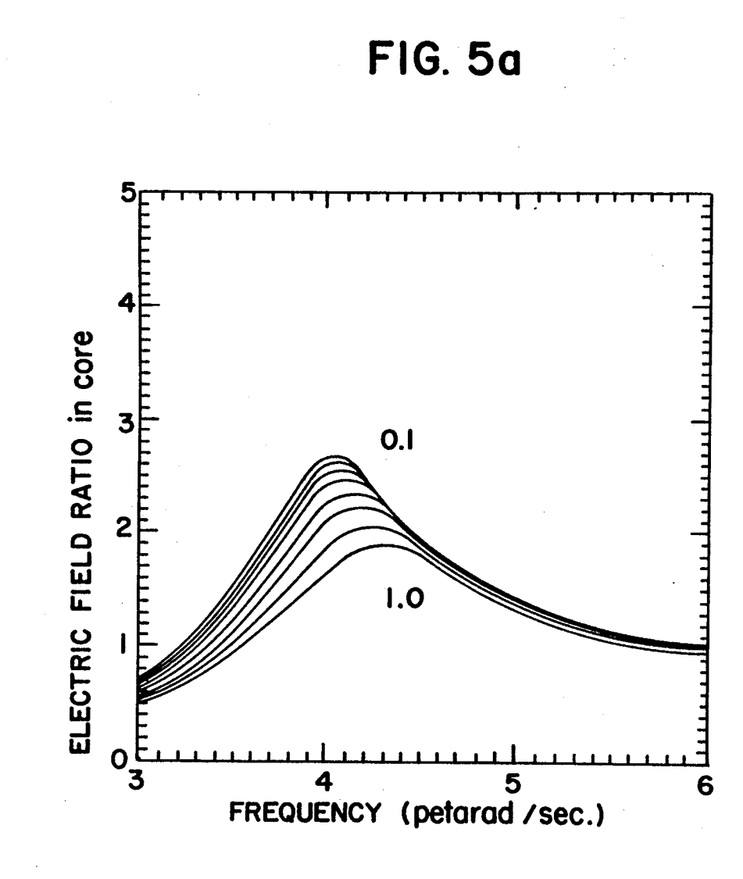
FIGS. 5a and 5b show the electric field ratio in the core of the composite, material for the first preferred embodiment.
Figure 5B:
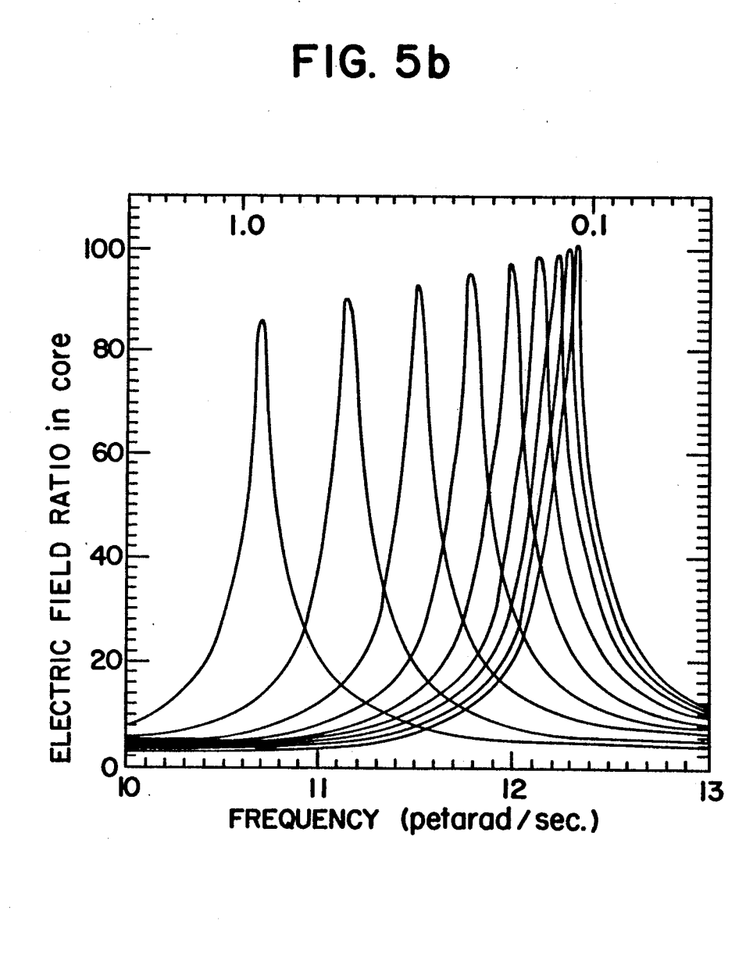

The magnitude of the electric field in the core region of the particle with gold and with aluminum cores are shown in FIGS. 5a and 5b as a function of frequency with the ratio $r_1/r_2$ as a parameter and with $r_1$ fixed at 5 nm. FIGS. 5a and 5b show the ratio of the electric field in the core $E_1$ to the electric field far from the structure $E_0$ as the ratio of core to shell radius $r_1/r_2$ varies from 0.1 to 1.0 with $r_1 = 5$ nm. FIG. 5a is for a gold core and FIG. 5b is for an aluminum core. The resonance frequency, $\omega_R$, may be shifted by altering the shell thickness to provide "tunability." When the permittivity $\epsilon_2$ is greater than $\epsilon_3$, then the resonance $\omega_r$ is shifted to lower frequency with increasing shell thickness; conversely if $\epsilon_2$ is less than $\epsilon_3$, then the resonance $\omega_R$ is shifted to higher frequency with increasing shell thickness. Resonant enhancement of the electric field is inversely related to $\epsilon_1''$; this key material parameter will optimize the enhancement. The spatial distribution of the magnitude of the electric field ratio for each region is shown in FIGS. 6a and 6b. The enhancement may also be improved by adjusting the temperature for minimum $\epsilon \propto$.

Figure 6A:
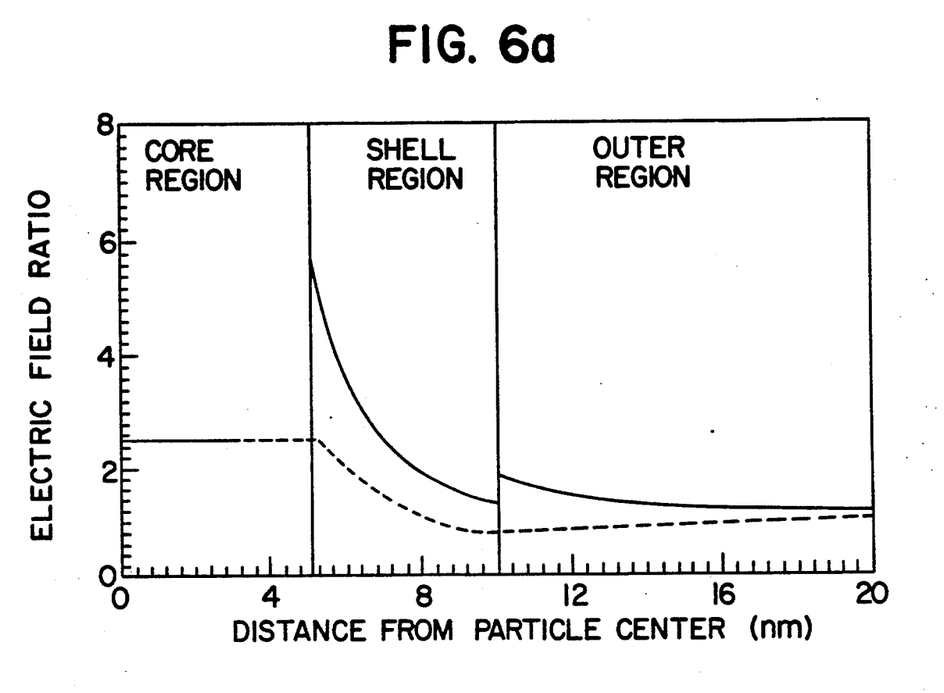
FIGS. 6a and 6b show the electric field ratio in and around a particle of the composite material for the first preferred embodiment.
Figure 6B:
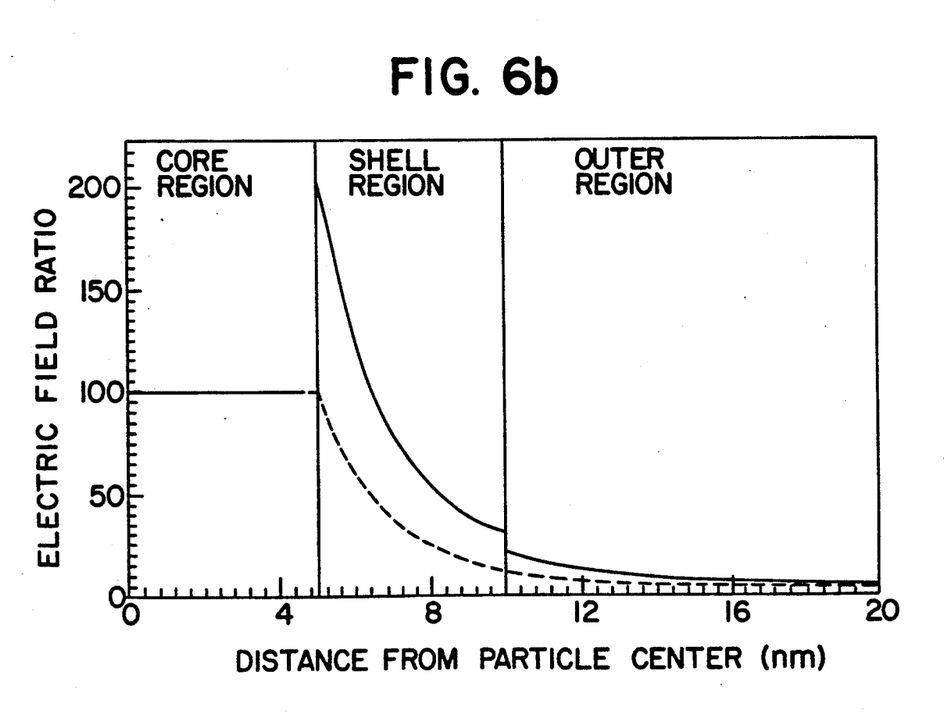

FIGS. 6a and 6b show the ratio of electric field in each region of the material relative to $E_0$ as a function of the distance from the center of the particle. The solid line is for electric field measurements parallel to $E_0$ and the dashed line is for measurement perpendicular to $E_0$. In FIG. 6a the core is gold, $\epsilon_1/\epsilon_0 = 5.3 + i2.5$, $\epsilon_2/\epsilon_0 = 2.5$, and $\epsilon_3/\epsilon_0 = 1.7$. In FIG. 6b, the core is aluminum, $\epsilon_1/\epsilon_0 = -2.5 + i0.042$, $\epsilon_2/\epsilon_0 = 1.2$ and $\epsilon_3/\epsilon_0 = 1.7$.

The electric field distribution concentrated in the neighborhood of the particle will affect the optical nonlinear behavior of the suspension. For an electrostrictive mechanism, a microparticle suspension subject to an optical field develops an effective $\chi^{(3)}$ due to electrostrictive forces proportional to the square of the polarizability and hence dipole moment. The increase in dipole moment of the particle at resonance given by equations 1, 2 and 3 will result in a substantial increase in the effective third order optical nonlinearity. A particle with a polystyrene or silica shell and with a gold core or with an aluminum core with $r_1/r_2 = 0.5$ will experience an enhancement of 18 or of 7200 in the effective $\chi^{(3)}$ over that of a pure polystyrene or pure silica particle; the corresponding enhancements in phase conjugate reflectivity would be 330 and $5 \times 10^7$, respectively. For gold shelled or aluminum shelled particles, the effective $\chi^{(3)}$ can be enhanced by $10^4$ at 500 nm with a time constant reduction factor of 10.

The electronic mechanism calculation for the particle is an extension of prior art treatments of metallic particles in a linear dielectric. The mean polarization and dielectric permittivity, $\epsilon$, of the composite considered homogeneous medium are related through $D = \epsilon E = \epsilon_0 E + P$ with the polarization $$P = \epsilon_0 \chi^{(1)} E + \epsilon_0 \chi^{(2)} E^2 + \epsilon_0 \chi^{(3)} E^3 \quad (4)$$

If this is expressed as $P = P_L + P_{NL}$ and $\epsilon = \epsilon_L + \epsilon$, then $P_{NL} = \delta\epsilon E$ with $\delta\bar{\epsilon} = \delta\epsilon_0 \chi^{(2)} E + \epsilon_0 X^{(3)} E^2$. The $\epsilon$ represents the field dependent perturbation of the medium treated as a continuum with E as the mean field; if $\delta\bar{\epsilon}$ is now considered as a function of the material composition variables, where the subscripts 1, 2, 3 refer to the core, shell and medium respectively $$\delta\bar{\epsilon} = \frac{\delta\bar{\epsilon}}{\delta\epsilon_1}\delta\epsilon_1 + \frac{\delta\bar{\epsilon}}{\delta\epsilon_2}\delta\epsilon_2 + \frac{\delta\bar{\epsilon}}{\delta\epsilon_3}\delta\epsilon_3 \quad (5)$$

The $\epsilon_1$, $\epsilon_2$, $\epsilon_3$ are the field dependent variations of each material component of the material obtained from the respective nonlinear susceptibilities by $\delta\epsilon_q = \epsilon_0\chi_q^{(3)}E_q^2$ with the localized field factors $f_{1q} = E_q/E_0$ and $q = 1, 2, 3$.

The dielectric constitutive equation for a dilute suspension of particles with no shell is taken as the Maxwell-Garnett form, which to the first order in $p$ becomes $$\bar{\epsilon} = \epsilon_3 + 3p\,\epsilon_3\,\frac{\kappa_{eff} - 1}{\kappa_{eff} + 2} \quad (6)$$

where $\kappa_{eff} = \epsilon_1/\epsilon_3$; whereas for the case of a dilute suspension of composite particles, $\kappa_{eff}$ is given by equation 3. The three partial derivatives required for equation 5 become $$\frac{\delta\bar{\epsilon}}{\delta\epsilon_q} = 9p\,\epsilon_3\,\frac{\frac{\delta\kappa_{eff}}{\delta\epsilon_q}}{(\kappa_{eff} + 2)^2} \quad \text{for } q = 1,2 \quad (7a)$$

$$\frac{\delta\bar{\epsilon}}{\delta\epsilon_3} = 1 + 3p\,\frac{(\kappa_{eff}^2 - 2\kappa_{eff} - 2)}{(\kappa_{eff} - 2)^2} \quad (7b)$$

The equivalent homogeneous field E is obtained by integration over the inhomogeneous sample to define a space averaged $f_3$, $E = f_3 E_o$. The total nonlinear polarization then becomes $$P_{NL} = \epsilon_o \sum_{i=1}^{3} f_3 f_{2q} \overline{f_{1q}^2} \chi_q^{(3)} E_o^3 \quad (8a)$$

where the $\overline{f_{1q}^2}$ are space averaged over the qth region. For a DFWM experiment in an isotropic medium in which the forward, back and probe input beams $E_f$, $E_b$, $E_p$ are all polarized in the same z direction, and since $E_o = E_f + E_b + E_p$, the z component of nonlinear polarization reduces to $$P_{zNL} = \tfrac{3}{2}\epsilon_o \chi_{zzzz}^{(3)} E_{fz} E_{oz} E_{pz}^* \quad (8b)$$

For this system the z component of field is dominant; so that the averages in equation 8a are taken over the z component of electric field to yield $$P_{NL} = \epsilon_o \sum_q \overline{f_3} f_{2q} \overline{f_{1q}^2} \chi_q^{(3)} E_f E_p E_p^* \quad (8c)$$

where $\chi_q^{(3)} = \tfrac{3}{2}\chi_{zzzz}$ with $q = 1 \ldots 3$. The intensity of the phase conjugate signal and hence reflectivity is proportional to the square of $P_{NL}$. The range of applicability of this dilute suspension theory is estimated at 10% by volume for 20 nm gold cored particles. This estimate is based on the criterion that the field $E_3$ should decay to within 5% of $E_o$ at the mean interparticle distance.

Figure 7A:
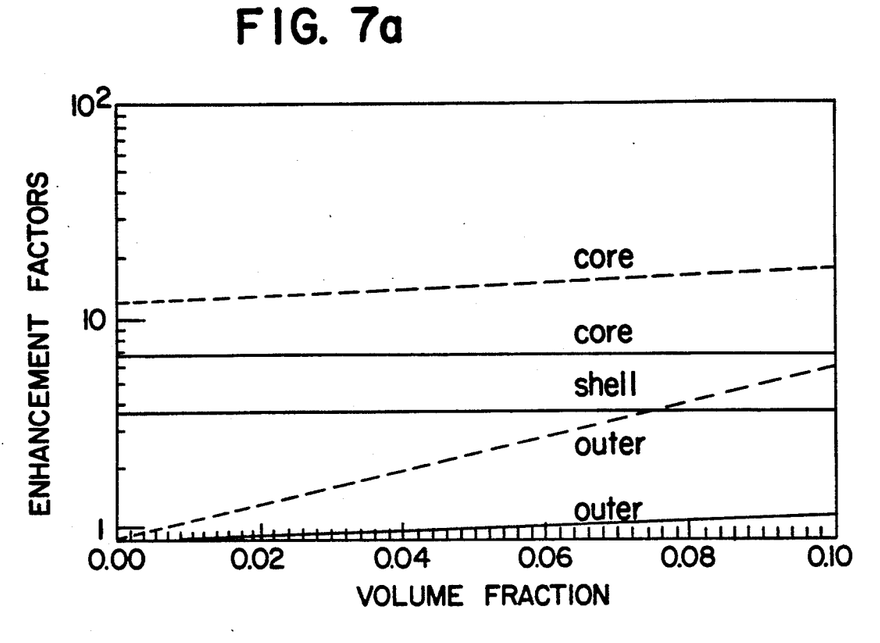
FIGS. 7a and 7b show the enhancement factor of $\chi^{(3)}$ versus particulate concentration for the first preferred embodiment.
Figure 7B:
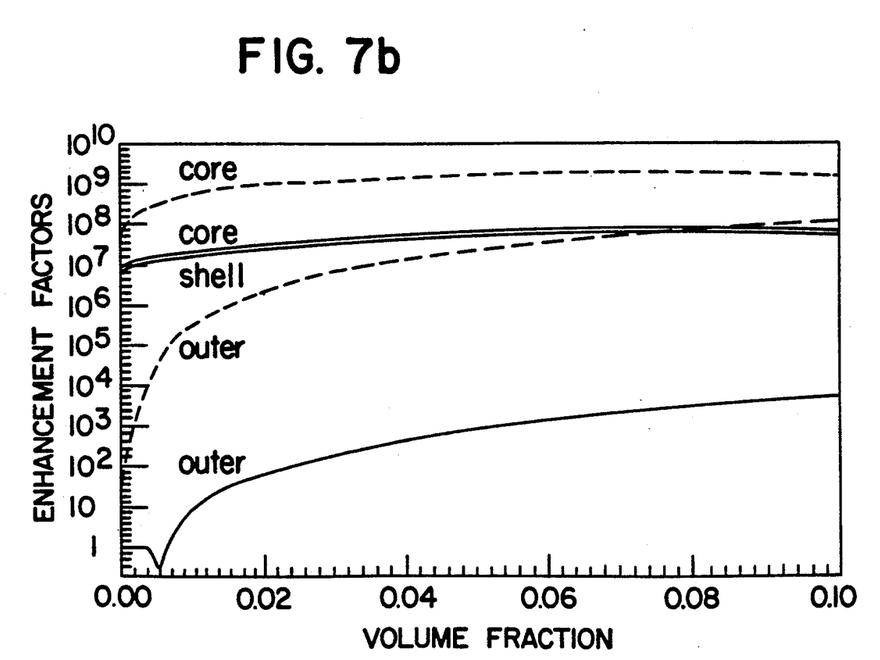

The results of the field concentrated in the neighborhood of the particle on the phase conjugate reflectivity for each combination of nonlinear core, shell, and suspension medium can be determined from FIGS. 7a and 7b for the given sample parameters. FIGS. 7a and 7b show the concentration dependence of the enhancement factor for the phase conjugate amplitude for the core, shell and outer region. The solid lines are for $r_1/r_2 = 0.5$ and the dashed lines are for $r_1/r_2 = 1.0$. FIG. 7a has a gold core and FIG. 7b has an aluminum core; the dielectric permittivities are as described in FIGS. 6a and 6b. The product field enhancement factor of equation 8 is plotted in these figures as a function of particle concentration, and can be used to examine various structures. By way of illustration similar figures are used to examine a few specific examples. In the ultraviolet at 200 nm., a 0.2% particulate concentration with an aluminum core and nonlinear urea shell, with $r_1/r_2 = 0.9$, suspended in a fused silica medium would exhibit an effective $\chi^{(3)} = 0.9 \times 10^{-7}$ esu compared to a homogeneous urea sample with $\chi^{(3)} = 1 \times 10^{-12}$ esu, and conjugate beam reflectivity enhancement of $0.8 \times 10^{10}$. In the visible at 488 nm., a nonlinear fluorescein doped borosilicate glass exhibits a (slow) $\chi^{(3)} = 1$ esu, whereas the fluorescein adsorbed to gold spheres at the same concentration should exhibit an effective $\chi^{(3)} = 4$ esu at the same speed, corresponding to a reflectivity enhancement of 16. Such samples might be prepared by using the metallic nanospheres as nucleating sites for controlled crystal growth or polymer adsorption sites.

Thus, as demonstrated above, in the present invention the electric field both interior and in the exterior neighborhood of the particle is increased at the plasmon resonance. The increased field is then utilized for enhancement of the intrinsic third order nonlinear susceptibilities of the core, shell and neighborhood or localized suspension medium. The increased electric field in the regions, and the resulting enhanced intrinsic third order nonlinear susceptibilities of the regions give rise to an enhanced effective third order nonlinear susceptibility of the material. This enhanced effective third order nonlinear susceptibility may be attributed partially to an electrostrictive mechanism acting on the material and partially to an electronic, excitonic, or any other intrinsic nonlinear mechanism acting on the material.

Furthermore, it is the imaginary component of the permittivity, usually $\epsilon_1''$ of the core material, that determines the magnitude of the field enhancement of the material. The plasmon resonance $\omega_R$ may be tuned by adjusting the ratio $r_1/r_2$ of the particle. That is, given $r_1$, $r_2$, $\epsilon_2$ and $\epsilon_3$, the dispersive dielectric function for the metal then determines the plasmon resonant frequency $\omega_R (r_1/r_2)$. Thus, the plasmon resonance can be tuned through adjustment of $r_1/r_2$.

In a second preferred embodiment, the material 32 of FIG. 4 consists of nanospheres 34 with a nonlinear core, $\epsilon_1$, and metallic shell, $\epsilon_2$, suspended in a nonlinear medium 36, $\epsilon_3$. The use of a metallic shell instead of a metallic core in the particle overcomes the frequency range restrictions imposed by the dielectric dispersion of the metal and therefore provides for a wide range of nonlinear materials. Calculations for gold and for aluminum shells indicate that phase conjugate reflectivity enhancements in excess of $10^8$ can be achieved.

In the first preferred embodiment of the composite materials, i.e., metal core and nonlinear dielectric shell particles in a nonlinear medium, the useful wavelength range of adjustment was sufficiently restricted so that a different metal was required for each spectral region. This can be seen in FIGS. 5a and 5b. The dual role of the metallic core was to provide the negative dielectric constant requisite for resonance and to act as a source term for the field distribution. These functions are separated in a particle in which a metallic shell surrounds a dielectric core and is suspended in a nonlinear medium. With this model a large spectral range can be achieved through adjustment or "tuning" of shell thickness even with a single metal and still derive large field enhancements.

In the second preferred embodiment of the composite materials, light of an optical frequency $\omega_R$, the surface-mode resonance of the material, is incident on the material, at the surface surface-mode resonance, resulting in an enhanced effective third order nonlinear susceptibility of the material. In the following description the suspensions are again considered to be sufficiently dilute so that interparticle effects may be neglected. It is further assumed in every case that the materials behave as linear dielectrics for the purpose of the localized electric field evaluation, and the nonlinear dielectric properties contribute only to calculation of the phase conjugate field. When intrinsic bistability considerations are involved $\epsilon_1 = \epsilon_1(E_1)$, $\epsilon_2 = \epsilon_2(E_2)$ and $\epsilon_3 = \epsilon_3(E_3)$.

Calculating the electric field distribution $\epsilon_1$, $\epsilon_2$ and $E_3$ for each region of the material $\epsilon_1$, $\epsilon_2$ and $\epsilon_3$, within the electrostatic approximation relative to the electric field $E_o$ far from the particle, $$\bar{E}_1 = \frac{9 \epsilon_2 \epsilon_3}{\epsilon_2 \epsilon_a + 2\epsilon_3 \epsilon_b} E_o [\cos\theta \, e_r - \sin\theta \, e_\theta] \tag{9a}$$

$$\bar{E}_2 = \frac{3 \epsilon_3 \epsilon_a(r)}{\epsilon_2 \epsilon_a + 2\epsilon_3 \epsilon_b} E_o \cos\theta \, e_r - \tag{9b}$$

$$\frac{3 \epsilon_3 \epsilon_b(r)}{\epsilon_2 \epsilon_a + 2\epsilon_3 \epsilon_b} E_o \sin\theta \, e_\theta$$

$$\bar{E}_3 = \left[ 2 \frac{\epsilon_2 \epsilon_a - \epsilon_3 \epsilon_b}{\epsilon_2 \epsilon_a - 2\epsilon_3 \epsilon_b} \frac{r_2^3}{r^3} + 1 \right] E_o \cos\theta \, e_r + \tag{9c}$$

$$\left[ \frac{\epsilon_2 \epsilon_a - \epsilon_3 \epsilon_b}{\epsilon_2 \epsilon_a - 2\epsilon_3 \epsilon_b} \frac{r_2^3}{r^3} - 1 \right] E_o \sin\theta \, e_\theta$$

where $$\epsilon_a(r) \equiv \epsilon_1[1 - 2(r_1/r)^3] + 2\epsilon_2[1 - (r_1/r)^3] \tag{10a}$$

$$\epsilon_b(r) \equiv \epsilon_1[1 - (r_1/r)^3] + \epsilon_2[2 + (r_1/r)^3] \tag{10b}$$

$$\epsilon_a \equiv \epsilon_a(r_2) \tag{10c}$$

$$\epsilon_b \equiv \epsilon_b(r_2) \tag{10d}$$

The condition for surface mediated plasmon resonance at a frequency $\omega_R$ is defined for the particle by setting the real part of the complex dielectric expression in the denominator of the field equations 9 to zero.

$$Re \, [\epsilon_2 \epsilon_a + 2\epsilon_3 \epsilon_b] = 0 \tag{11a}$$

If only the metallic shell, $\epsilon_2$, is taken as complex, and $P = 1 - (r_1/r_2)^3$, then this resonance condition becomes $$2\epsilon_2' P = -3[\epsilon_1 + 2\epsilon_3] + 2[\epsilon_1 + \epsilon_3]P - 2[(\epsilon_1\epsilon_3 - \epsilon_2''^2)/\epsilon_2'] P \tag{11b}$$

The resonance equation is solved for any ratio $r_1/r_2$ given $\epsilon_1$ and $\epsilon_3$ to obtain the requisite negative $\epsilon_2'$. The dispersive dielectric function for the metal then determines the plasmon resonant frequency $\omega_R (r_1/r_2)$. For example, a theoretical model such as the Drude-Lorentz function for free plus bound electron contributions $$\epsilon_2(\omega) = \epsilon_o \left( 1 - \omega_{pf}^2 \frac{1}{\omega^2 + f\omega\gamma_f} + \omega_{pb}^2 \frac{1}{\omega_o^2 - \omega^2 - i\omega\gamma_b} \right) \tag{12}$$

can describe the dielectric function for metallic gold or an empirical function can be fit to the experimental data. The parameters of the model are $\omega_{pf}$ and $\omega_{pb}$, the free and bound plasmon frequencies; $\tau_f$ and $\tau_b$, the free and bound electron decay rates; and $\omega_o$, the bound electron resonant frequency.

Figure 8A:
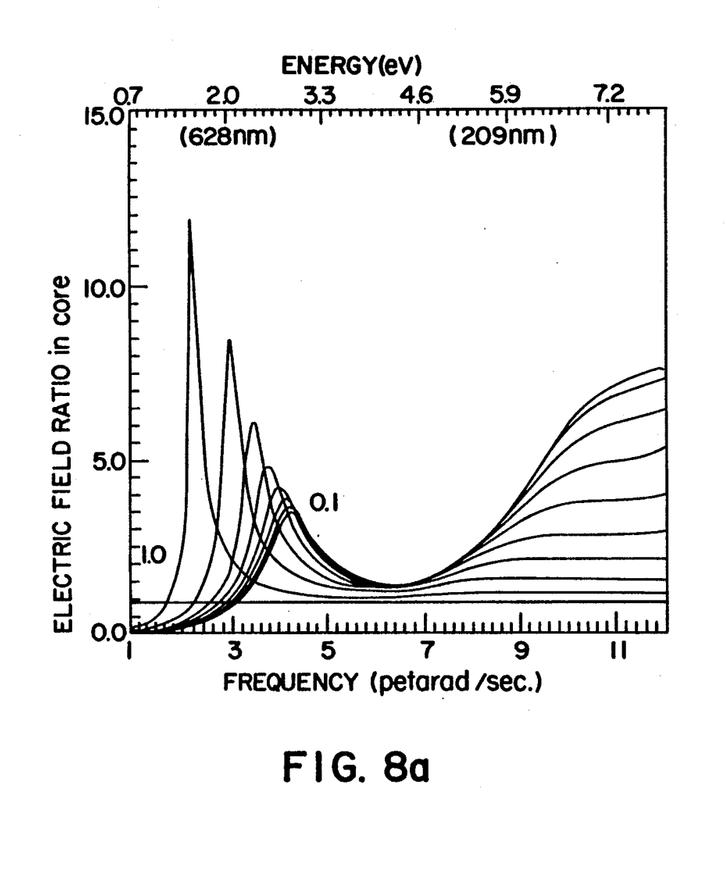
FIGS. 8a and 8b show the electric field ratio in the core of the composite material particles of the second preferred embodiment.
Figure 8B:
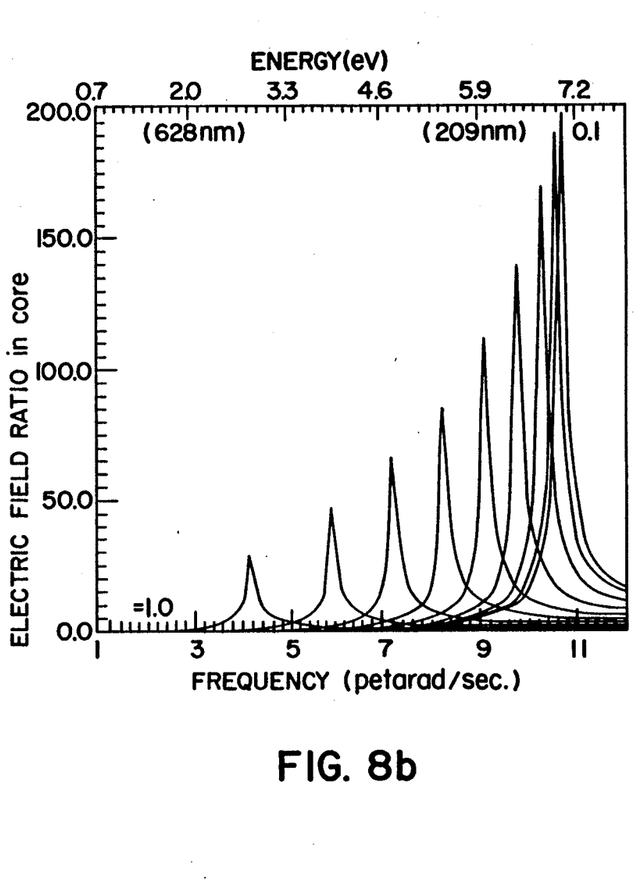
Figure 9A:
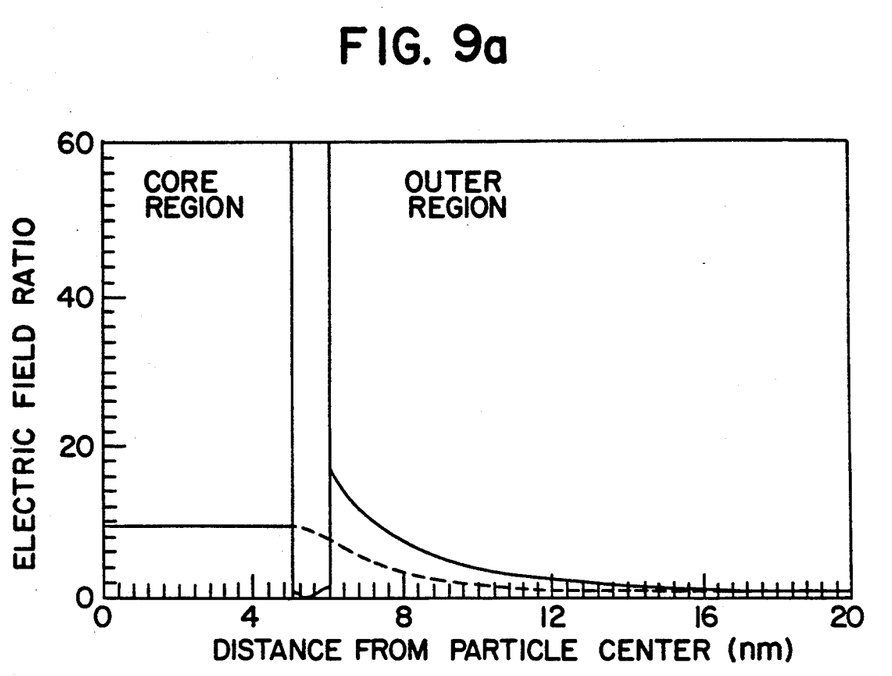
FIGS. 9a and 9b show the electric field ratio in and around a particle of the composite material for the second preferred embodiment.
Figure 9B:
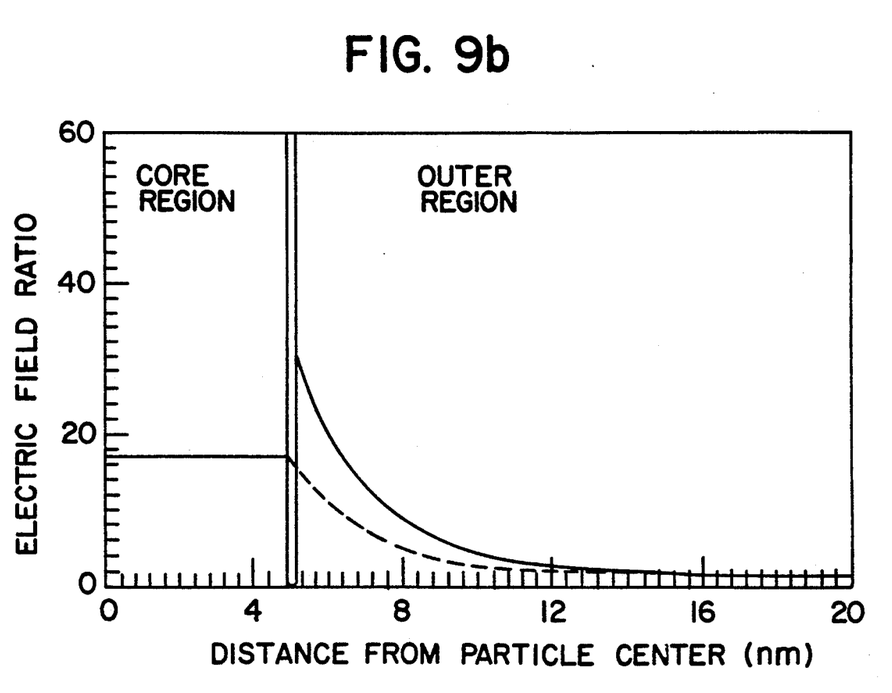

The resonant behavior of the electric field in the core dielectric region of the composite particles with gold and with aluminum shells are shown in FIGS. 8a and 8b with the ratio $r_1/r_2$ as a parameter. FIGS. 8a and 8b show the magnitude of the electric filed ratio $E_1/E_0$ in the core region as a function of frequency. The ratio $r_1/r_2$ varies from 0.1 to 1.0 and $\epsilon_1/\epsilon_0=2.5$ and $\epsilon_3/\epsilon_0=1.7$. In FIG. 8a the shell is gold and is fitted to the Drude-Lorentz model with $\omega_{pf}=1.3 \cdot 10^{16}$, $\tau_f=9.3 \cdot 10^{-15}$, $\omega_{pb}=7 \cdot 10^{15}$ and $\tau_b=2.2 \cdot 10^{-16}$. In FIG. 8b the shell is aluminum and is fitted to the Drude model with $\omega_{pf}=2.28 \cdot 10^{16}$ and $\tau_f=6.9 \cdot 10^{-15}$. These curves illustrate the high degree of "tunability" of $\omega_R$ that can be attained by altering the shell thickness. Tunability of $\omega_R$ from ultraviolet to infrared is predicted. Comparison of FIGS. 8a and 8b also indicate that in FIG. 8a a broadband near-resonance could be obtained. Complementary matching of dielectric and metallic dielectric functions could make the particles very broad-band. The magnitude of the field enhancement at resonance depends inversely on the dielectric loss at each wavelength. Examples of the spatial distribution of the magnitude of the electric field at resonance in the core, shell, and outer region for each particle is shown in FIGS. 9a and 9b. FIGS. 9a and 9b show the ratio of electric field in each region to $E_0$ as a function of distance from the center of the particle. The solid line is for the measurement of electric filed taken parallel to $E_0$ and the dashed line is for the filed taken perpendicular to $E_0$. The resonant frequency in both figures is $2.8 \cdot 10^{15}$ Hz. FIG. 9a is a gold shell with $r_1/r_2=0.83$ and $\epsilon_2/\epsilon_0=-16.77+i1.98$. FIG. 9b is an aluminum shell with $r_1/r_2=0.955$ and $\epsilon_2/\epsilon_0=-65.1+i3.4$. The principle observation is that large enhancement can be attained in the core and outer region at the expense of the field in the shell due to the two metal dielectric boundary conditions.

Enhancement of the effective third order optical nonlinear susceptibility $\chi_{eff}^{(3)}$ is a result of the field concentrated in the neighborhood of the particle at the surface mediated resonance. Two different mechanisms for $\chi^{(3)}$ are described, the electrostrictive mechanism and the electronic mechanism. In the electrostrictive mechanism, a microparticle suspension subject to gradients in the electromagnetic field develops an effective third order optical nonlinearity due to electrostrictive forces given by $$\chi_{eff}^{(3)} = \frac{12\pi\epsilon_3}{k_b T} \rho \, r_2^3 \left[ \frac{\epsilon_2\epsilon_a - \epsilon_3\epsilon_b}{\epsilon_2\epsilon_a + 2\epsilon_3\epsilon_b} \right]^2 \quad (13)$$

where is the volume fraction of particles. Thus the increase in the polarizability of the particle at the plasmon resonance condition will result in a substantial increase in $\chi_{eff}^{(3)}$.

For the electronic mechanism, calculation of $\chi_{eff}^{(3)}$ for the particle is similar to the first preferred embodiment for metallic core particles described above. The inhomogeneous material with core, shell and suspending medium dielectric permittivities, $\epsilon_q$, and intrinsic nonlinear susceptibilities $\chi_q^{(3)}$ where $q=1, 2$, and 3 respectively is represented as an equivalent homogeneous medium of $\epsilon$ and $\chi_{eff}^{(3)}$. The dielectric constitutive equation for $\epsilon$ for a dilute suspension of composite particles is of the Maxwell-Garnett form to the first order in $\rho$.

$$\bar{\epsilon} = \epsilon_3 + 3\rho \, \epsilon_3 \frac{\epsilon_2\epsilon_a - \epsilon_3\epsilon_b}{\epsilon_2\epsilon_a + 2\epsilon_3\epsilon_b} \quad (14)$$

For a degenerate four-wave mixing (DFWM) experiment in an isotropic medium in which the forward, back and probe input beams $E_f$, $E_b$, $E_p$ are all polarized in the same z direction, and since $E_o=E_f+E_b+E_p$, the z component of nonlinear polarization reduces to $$P_{NL} = \epsilon_o \sum_q \bar{f_3} \, f_{2q} \bar{f_{1q}^2} \, \chi_q^{(3)} \, E_f E_b E_p^* \quad (15)$$

where $\chi_q^{(3)} = \frac{3}{4}\chi_{zzzz}$ with $q=1 \ldots 3$. The local field factors $f_{1q}$, the three concentration dependent partial derivatives $f_{2q}$, and the factor $f_3$ obtained by integration over the inhomogeneous sample to define the equivalent homogeneous field E, are given relative to $E_o$ far from the particle by $$E_q = f_{1q}(r)E_o \quad (16a)$$

$$f_{2q} \equiv \frac{\partial \bar{\epsilon}}{\partial \epsilon_a} \quad (16b)$$

$$E \equiv \bar{f_3} E_0 \quad (16c)$$

The average factors $\bar{f_{1q}^2}$ and $\bar{f_3}$ are obtained by integration on the z component of the electric field over each region q of the material. The contribution from the other components of the inhomogeneous field in the tensorial integration have been neglected either on the basis of small magnitude or because we ignore the deplorized component of polarization. The product enhancement factors $f_{4q}$ and $\chi_{eff}^{(3)}$ of the total material on comparison to equation 8 are defined by $$P_{NL} = \epsilon_o \chi_{eff}^{(3)} E_f E_b E_p^* \quad (17)$$

$$f_{4q} \equiv \bar{f_3} f_{2q} \bar{f_{1q}} \quad (18)$$

$$\chi_{eff}^{(3)} = \Sigma f_{4q} \chi_q^{(3)} \quad (19)$$

Figure 10A:
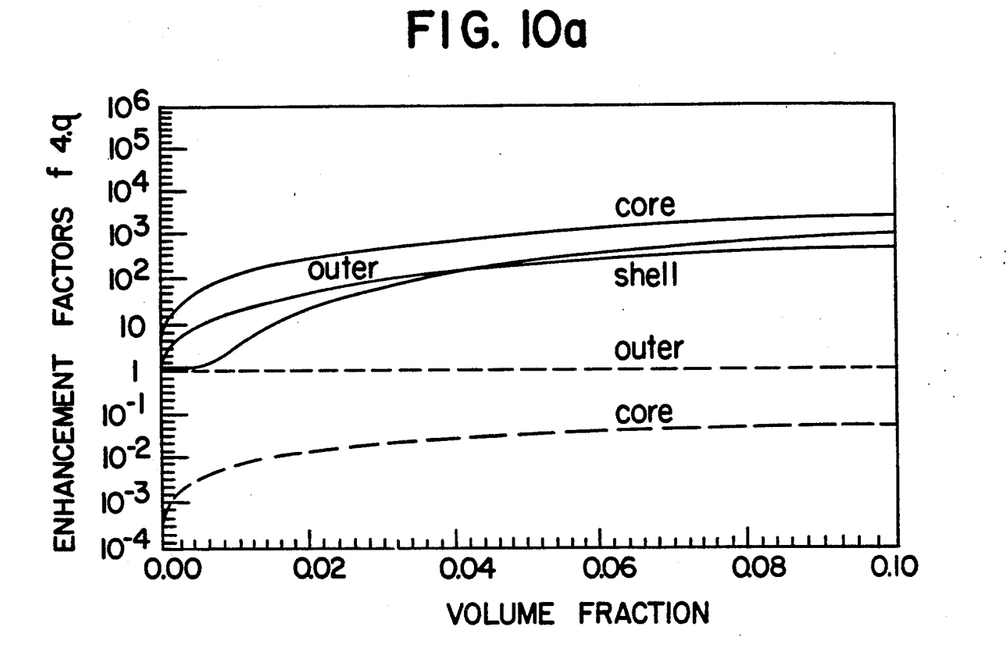
FIGS. 10a and 10b show the enhancement factor of $\chi^{(3)}$ versus particulate concentration for the second preferred embodiment.
Figure 10B:
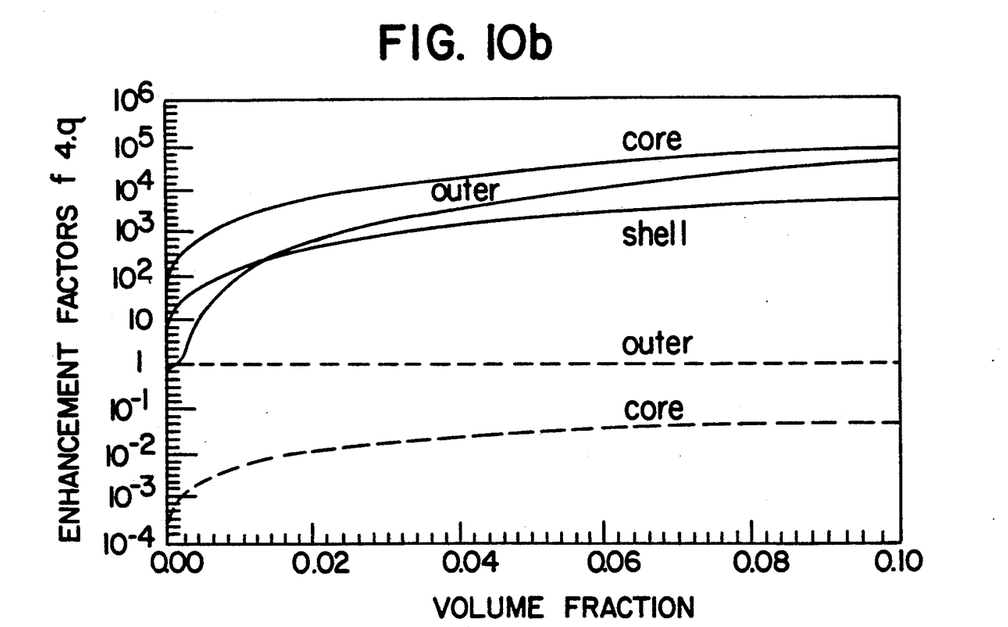

An example of the $f_{4q}$ enhancement factors for composites with a gold shell and for composites with an aluminum shell as a function of concentration are seen in FIGS. 10a and 10b. FIGS. 10a and 10b show the concentration dependence of the enhancement factor $f_{4q}$ for the phase conjugate amplitude for the core, shell and outer region. The solid lines are for $r_1/r_2=0.5$ and the dashed lines are for $r_1/r_2=1.0$ as in FIGS. 7a and 7b. the dielectric permittivities are as given in FIGS. 6a and 6b. FIG. 10a shows a gold shell composite and FIG. 10b shows an aluminum shell composite.

Thus, in the second preferred embodiment of the composite materials a metallic clad dielectric cored particle is used to increase the electric field in the core and neighboring or localized nonlinear medium at the plasmon resonance frequency. The increased field in the vicinity of the particle enhances the intrinsic third order susceptibility of the core, shell and local suspension medium and therefore enhance the effective third order susceptibility for the material. Enhancements of reflectivity in excess of $10^8$ are predicted for both electrostrictive and electronic nonlinear mechanisms, with no change in the speed of the intrinsic nonlinearity. The resonant frequency $\omega_R$ is tunable from the ultraviolet to the infrared and complementary matching of materials can lead to a wide pass-band. The magnitude of the resonant enhancement of the field varies inversely with the metallic $\epsilon''$.

The particles and materials of the present invention have an enhanced figure of merit $\eta$. The figure of merit is given by the equation $$\eta = \frac{12\pi}{\eta_o} \frac{\chi^{(3)}}{\gamma} \quad (20)$$

The $\chi^{(3)}$ is the 3rd order intrinsic nonlinearity for a homogeneous material and is $\chi^{(3)}_{eff}$ of the composite material. $\gamma$ is the absorption of the composite material and comprises the sum of the intrinsic molecular absorption coefficient of the material $\gamma m$ and the scattering absorption coefficient of the material is $\gamma s$. $\eta_o$ is the effective refractive index of the material.

Since the figure of merit is thus proportional to the ratio of $\chi^{(3)}_{eff}$ to $\gamma$, the optical absorption of the composite material is required in order to establish a figure of merit for device utilization of the material.

In calculations using particles consisting of gold or aluminum and a nonlinear polymer such as PDA or PBA or urea and a linear medium, a figure of merit enhancement of up to $10^3$ is predicted. Such enhancements of n have been indirectly detected experimentally, as the phase conjugate signal to noise ratio for composite materials of the present invention have improved.

The figure of merit is important in phase conjugate mirror (PCM) applications, since for a DWFM PCM, $R = 0.131 \eta^2 l^2 / (n^2 \lambda^2)$.

The composite materials of the present invention are not limited to the use of spherical shaped particles suspended in a medium as described above. Any geometric arrangement of particles that will result in the third order nonlinear enhancement may be utilized. The core $\epsilon_1$ may be metal and the shell $\epsilon_2$ may be a nonlinear dielectric, or vice versa. The suspension medium $\epsilon_3$ may be linear or nonlinear dielectric material.

In each of the above embodiments, a "metal" core or shell of the particle includes "metal-like" or any material with a negative dielectric constant, and so can include superconductors or some materials with an anomalous dispersion or heavily doped semiconductors where free carrier motion dominates the dielectric function or conducting polymers. High temperature semiconductor will exclude field in the far IR, therefore the field will be concentrated at the exterior surface, which is where the nonlinear dielectric should be. An additional metallic shell will also cause plasmon resonance enhancement of the field in the nonlinear dielectric.

The materials and particles of the present invention may be applied as phase conjugate mirrors or a nonlinear evanescent wave switch. Its use in biopolymer characterization is also possible where the plasmon resonance would be selected to overlap any spectroscopic feature in dilute suspension, resulting in enhancement of the concentration sensitivity for detection. Used in a liquid scintillation counter, metallic labelled scintillators should be more efficient in photon capture.

Further, the application of the invention to light activated drugs is possible. If a metallic label is attached to 8-MOP, the UV dosage required for patient irradiation is reduced because radiation is localized to the required site.

Further, application of the invention to photodetector resolution will provide greater spatial decoupling through field localization. Field localization would also provide higher video disc resolution.

The present invention may also be applied to pulsed laser initiated nuclear fusion. The localized laser field enhancement on a scale smaller than the diffraction limit will lower laser power threshold for metallic coated nanoparticle implosion.

Application of the materials and particles of the present invention to a phase conjugate SBS mirror is possible. The piezo-optical effect is proportional to the localized field squared. Thus, the threshold for SBS can be lowered by a nanoparticle of metallic clad electrooptic materials.

The materials and particles of the present invention may also be used in laser velocimetry. The high scattering cross-section of composite particles at plasmon resonance permits smaller particles or lower concentrations that have smaller perturbation or flow properties.

In additional, a nonlinear waveguide material may also be formed by the materials and particles of the present invention. Such a waveguide may consist of three material layers index n1, a linear dielectric film; n2, the nonlinear composite; and n3, a linear dielectric substrate. The nonlinear composite n2 can be a suspension of any of the particles or the multilayer composite structure. Enhanced nonlinearity results.

Application of the materials and particles of the present invention to an extrinsic bistable or optical switch material is also possible. The composite material would lie between the plane dielectric mirrors in Fabry Perot geometry. The composition of the composite can be selected for sharpness of the plasmon resonance condition to attain high switching sensitivity. Planar geometry Fabry Perot structures are also possible.

Application of the materials and particles of the present invention to an intrinsic bistable or optical switch material is also possible. The composite particles of the present invention with nonlinear dielectric core suspended in a nonlinear dielectric have intrinsic bistability. The sharper plasmon resonance and the larger $\chi^{(3)}$ attainable would enormously enhance the switching sensitivity. Planar geometry intrinsic bistability is also possible. Moreover, a Mach Zender optical switch, where one leg is a nonlinear composite, can also be fabricated with the inventive optical structure. In addition, laser hardening is also possible, since a bistable material has a low level to transmit and a high level to reflect.

The materials and particles of the present invention may also be used to fabricate an intensity dependent narrow bandpass filter. In a laser hardening application, a Fabry Perot configuration would be required. For SBS geometry with the composite material, there is normal transmission at low intensity and SBS at high intensity. Depending on the composite choice, the filter could be made narrow band tunable or broad band tunable.

Application of the materials and particles of the present invention to a detector hardening material is also possible. Only a low intensity prescribed narrow band signal will reach the detector. The detector hardening material would exhibit enormous dynamic range. The input signal would pass through a beam splitter to a DFWM phase conjugate mirror (PCM) The PCM would be designed for a low saturation level and reflectivity of one up to saturation. The phase conjugate of the input is sent to the beam splitter and on to the detector only up to the threshold level. The PCM is narrow band because of the DFWM configuration.

In a nonlinear optical switching material, two prisms could be coupled by an evanescent wave through the material and particles of the present invention. The wave would either be transmitted or reflected depending on intensity.

Use of the materials of the present invention for harmonic generation is also possible. Input light of frequency would be localized in the material and particles and absorbed at the plasmon resonance frequency. The material and particles would remain highly transparent at harmonics of the resonant frequency. The variables available in the material and particles design permit choice of materials to satisfy the phase matching. The relevant $\chi^{(2)}$ and $\chi^{(3)}$ are enhanced, so that harmonic generation at lower power levels should be possible.

Use of the materials and particles of the present invention for an optical memory material is also possible. The particles act as huge super-dipoles at plasmon resonance. In high concentration, the asymmetric nano particles can experience optically induced ordering or phase transitions which lead to an optical memory material.

The present invention may also be applied to an optical amplifier material by means of the usual DFWM geometry.

The materials and particles of the present invention may be applied to the following devices which utilize a third order nonlinear response: a laser frequency converter device, an optical Kerr effect device, an electro-optical Kerr effect device, a four wave mixing composite device, an optical inteferometric waveguide gate device, a wide-band electrooptical guided-wave analog-to-digital converter device, an all-optical multiplexer device, an all optical demultiplexer device, an optical bistable device, an optical parametric device, and an optical fiber which is clad with a transparent coating.

Furthermore, in biopolymer characterization, gold spheres are now used as labels attached to biopolymers in optical and election microscopy. But, if plasmon resonance were selected to overlap any spectroscopic feature in dilute suspension, then concentration sensitivity for detection would be enhanced. This would apply to SERS, to molecular absorption spectra, to flourescence, to UV and IR spectroscopy.

The nanoparticles of the present invention may be fabricated using molecular beam epitaxy technology or chemical-vapor deposition technology. Layered Al—Si and Al—GaAs nanospheres have been fabricated in this manner.

Alternatively, nanoparticles may be fabricated by spinning, coating and evaporating. A polished glass substrate may be mounted on the axis of a high speed centrifuge. Two syringes provide fluid drops to the spinning surface. One syringe has a metallic plating solution, the other a nonlinear material in solution or suspension. The fluids spread and evaporate on the spinning substrate in one or more layers.

Before forming the metal shell about the nonlinear dielectric core, pretreating and filling all interstitial spaces in the core with neutral space filling atoms may be desirable. The metallic coating, for example, silver, will then stay on the core surface and be hindered from penetration into the core.

Similarly, a nonlinear dielectric core may be surface coated by charge adhesion of a layer of metallic nanoparticles, rather than atomic metal reduction at the surface. The surface tension would keep the metallic nanoparticle, for example, gold, intact rather than atomically dispersed in the core.

The optical particles of the present invention may have a semiconductor core as a "metallic" core under the broad definition of metal. More particularly, semiconductor nanocrystals of $CdS_xSe_{1-x}$ may be used. Also, superconductors may be used as the metallic core.

A metallic core with a semiconductor shell may also comprise the composite particles.

The optical particles of the composite materials, including cores of semiconductor material such as GaAs, may be suspended in a medium consisting of silicate glass or a polymeric glass such as polystyrene to form the composite materials of the inventor.

The nonlinear polymers such as polydiacetylene and polybenzothiazole can be used as the suspending medium of the composite materials or in the nanoparticle.

The suspending medium of the composite materials may also be a glass or crystal or some more complex superstructure.

The same concepts developed herein apply to magnetic as well as electric field terms in nonlinear polarization:

$$DNL = \chi_{ijk} \nabla E + \chi_{ijk} EE + \chi_{ijk} EB +$$
$$\chi_{ijkl} EEE + \chi_{ijkl} EBB + \ldots$$

where $\chi_{ijk}$ would be the magnetic-equivalent of $\chi^{(2)}$, and $\chi_{ijkl}$ would be the magnetic equivalent of $\chi^{(3)}$. The magnetic B fields are part of the optical filed or can be internal or external fields.

While the invention has been particularly shown and described with respect to illustrative and preferred embodiments thereof, it will be understood by those skilled in the art that the foregoing and other changes in form and details may be made without departing from the spirit and scope of the invention which should only be limited by the scope of the appended claims.

What is claimed is:

1. A particle comprising a core surrounded by a shell, one of said core and shell comprising a dielectric material exhibiting a third order nonlinear optical response when light is incident thereon and the other of said core and shell being a metal.

2. A particle as in claim 1 wherein said core is a metal and said shell is a dielectric exhibiting a third order nonlinear optical response when light is incident thereon.

3. A particle as in claim 2 wherein said particle exhibits an enhanced effective third order nonlinear response when light of at least one predetermined optical frequency is incident thereon.

4. A particle as in claim 2 wherein said dielectric shell comprises a region of a dielectric medium immediately adjacent a metal core suspended in said medium, said medium exhibiting a third order nonlinear response when light is incident thereon.

5. A particle as in claim 1 wherein said shell is a metal and said core is a dielectric exhibiting a third order nonlinear response when light is incident thereon.

6. A particle as in claim 5 wherein said particle exhibits an enhanced effective third order nonlinear response when light of at least one predetermined optical frequency is incident thereon.

7. A particle as in claims 1, 2 or 5 wherein said particle is a nanoparticle.

8. A particle as in claim 7 wherein said nanoparticle is a nanosphere.

9. A particle as in claim 7 wherein said nanoparticle is a nanoellipsoid.

10. A particle as in claim 7 wherein said nanoparticle is a nanocylinder.

11. A particle as in claim 1 wherein said dielectric material is one of polydiacetylene, polybenzothiazole, polystyrene and silica.

12. A particle as in claim 1 wherein said metal has dielectric permittivity less than zero.

13. A particle as in claim 1 wherein said metal is one of gold, aluminum and silver.

14. A particle as in claim 1 wherein said metal is a doped semiconductor.

15. A particle as in claims 1 wherein said metal is a superconductor.

16. A particle comprising a metal core surrounded by two or more shells, at least one of said two or more shells being a dielectric material exhibiting a third order nonlinear response when light is incident thereon.

17. A particle comprising a core surrounded by two or more shells, said core being a dielectric material exhibiting a third order nonlinear optical response when light is incident thereon, at least one of said two or more shells being a metal.

18. A particle as in claim 16 wherein all of said two or more shells are dielectric material exhibiting a third order nonlinear response when light is incident thereon.

19. A particle as in claim 16 wherein adjacent shells of all of said two or more shells alternate between metal and dielectric material exhibiting a third order nonlinear response when light is incident thereon.

20. A particle as in claim 17 wherein all of said two or more shells are metal.

21. A particle as in claim 17 wherein adjacent shells of all of said two or more shells alternate between metal and dielectric material exhibiting a third order nonlinear response when light is incident thereon.

22. A particle as in claims 16 or 17 wherein said particle exhibits an enhanced effective third order nonlinear response when light of at least one optical frequency is incident thereon.

23. A particle as in claims 16 or 17 wherein said metal has dielectric permittivity less than zero.

24. A particle as in claims 16 or 17 wherein said particle is a nanoparticle.

25. A particle as in claim 24 wherein said nanoparticle is one of a nanosphere, nanoellipsoid and a nanocylinder.

26. A composite material comprising a plurality of particles in a medium, each of said particles comprising a core surrounded by a shell, one of said core and shell comprising a dielectric material exhibiting a third order nonlinear optical response when light is incident thereon and the other of said core and shell being a metal.

27. A composite material as in claim 26 wherein said core is a metal and said shell is a dielectric exhibiting a third order nonlinear optical response when light is incident thereon.

28. A composite material as in claim 27 wherein said shell is a metal and said core is a dielectric exhibiting a third order nonlinear optical response when light is incident thereon.

29. A composite material as in claim 27 wherein said material exhibits an enhanced effective third order nonlinear response when light of at least one optical frequency is incident thereon.

30. A composite material as in claim 28 wherein said material exhibits an enhanced effective third order nonlinear response when light of at least one optical frequency is incident thereon.

31. A composite material as in claims 26, 27 or 28 wherein each of said particles are a nanoparticle.

32. A composite material as in claim 31 wherein each of said nanoparticles is one of a nanosphere, nanoellipsoid and nanocylinder.

33. A composite material as in claim 26 wherein said dielectric material is one of polydiacetylene, polybenzothiazole, polystyrene and silica.

34. A composite material as in claim 26 wherein said metal is one of gold, aluminum and silica.

35. A composite material as in claim 26 wherein said metal is a doped semiconductor.

36. A composite material as in claim 26 wherein said metal is a superconductor.

37. A composite material as in claim 26 wherein said metal has dielectric permittivity less than zero.

38. A composite material as in claim 26 wherein said medium exhibits a third order nonlinear response when light is incident thereon.

39. A composite material as in claim 38 wherein said medium is one of polydiacetylene and polybenzothiazole.

40. A composite material as in claim 38 wherein said medium is a polymeric glass.

41. A composite material as in claim 26 wherein said medium is glass.

42. A composite material as in claim 26 wherein said medium is water.

43. A composite material comprising a plurality of particles suspended in a medium, each of said particles comprising a metal core surrounded by two or more shells, at least one of said two or more shells being a dielectric material exhibiting a third order nonlinear response when light is incident thereon.

44. A composite material comprising a plurality of particles suspended in a medium, each of said particles comprising a core surrounded by two or more shells, said core being a dielectric material exhibiting a third order nonlinear optical response when light is incident thereon, at least one of said two or more shells being a metal.

45. A composite material as in claims 43 or 44 wherein said material exhibits an effective third order nonlinear response when light of at least one predetermined optical frequency is incident thereon.

46. A composite material as in claims 43 or 44 wherein each of said particles is a nanoparticle.

47. A composite material as in claim 46 wherein each of said nanoparticles is one of a nanosphere, nanoellipsoid and nanocylinder.

48. A composite material as in claims 43 or 44 wherein adjacent shells of said two or more shells alternate between metal and dielectric material exhibiting a third order nonlinear response when light is incident thereon.

49. A composite material as in claims 43 or 44 wherein said medium exhibits third order nonlinear response when light is incident thereon.

50. A composite material as in claims 43 or 44 wherein said metal has dielectric permittivity less than zero.

51. A composite material as in claim 29 wherein said enhanced response occurs when $K'_{eff}+2=0$.

52. A composite material as in claim 30 wherein said enhanced response occurs when $$2\epsilon_2' = -3[\epsilon_1+2\epsilon_3]+2[\epsilon_1+\epsilon_3]-2[\epsilon_1\epsilon_3-\epsilon_2''^2]/\epsilon_2'].$$

* * * * *

UNITED STATES PATENT AND TRADEMARK OFFICE
CERTIFICATE OF CORRECTION

PATENT NO. : 5,023,139

DATED : June 11, 1991

INVENTOR(S) : Meyer H. Birnboim, et al.

It is certified that error appears in the above-identified patent and that said Letters Patent is hereby corrected as shown below:

Column 11, line 5: "filed" should read as --field--

Column 11, line 29: "filed" should read as --field--

Column 11, line 30: "filed" should read as --field--

Column 12, line 43: "$\overline{f_{1q}}$" should read as --$\overline{f_{1q}^2}$--

Column 16, line 36, "fields" should read as --field--

Column 17, line 20, Claim 15: "claims 1" should read as --claim 1--

Signed and Sealed this

Ninth Day of March, 1993

*Attest:*

STEPHEN G. KUNIN

*Attesting Officer*   *Acting Commissioner of Patents and Trademarks*